(12) United States Patent
Fang et al.

(10) Patent No.: US 9,587,267 B2
(45) Date of Patent: Mar. 7, 2017

(54) QUANTIFICATION OF NUCLEIC ACIDS

(75) Inventors: Nan Fang, Neuss (DE); Andreas Missel, Düsseldorf (DE); Dirk Löffert, Düsseldorf (DE)

(73) Assignee: QIAGEN GMBH, Hilden (DE)

( * ) Notice: Subject to any disclaimer, the term of this patent is extended or adjusted under 35 U.S.C. 154(b) by 272 days.

(21) Appl. No.: 13/255,696

(22) PCT Filed: Mar. 9, 2010

(86) PCT No.: PCT/EP2010/052989
§ 371 (c)(1),
(2), (4) Date: Dec. 21, 2011

(87) PCT Pub. No.: WO2010/103010
PCT Pub. Date: Sep. 16, 2010

(65) Prior Publication Data
US 2012/0107813 A1    May 3, 2012

(30) Foreign Application Priority Data
Mar. 10, 2009    (DE) .......... 10 2009 012 039

(51) Int. Cl.
*C12P 19/34* (2006.01)
*C12Q 1/68* (2006.01)
*C07H 21/02* (2006.01)
*C07H 21/04* (2006.01)
*C07H 21/00* (2006.01)

(52) U.S. Cl.
CPC .................. *C12Q 1/6806* (2013.01)

(58) Field of Classification Search
USPC ............ 435/6.1, 6.11, 6.12, 91.1, 91.2, 183; 436/94, 501; 536/23.1, 24.3, 24.33, 25.3; 514/3.2
See application file for complete search history.

(56) References Cited

U.S. PATENT DOCUMENTS

| 4,683,195 | A | * | 7/1987 | Mullis et al. | ........ 435/6.11 |
| 2005/0266417 | A1 | * | 12/2005 | Barany et al. | ........ 435/6 |
| 2006/0115847 | A1 | * | 6/2006 | Andersen et al. | ........ 435/6 |
| 2008/0108063 | A1 | * | 5/2008 | Lucero et al. | ........ 435/6 |

FOREIGN PATENT DOCUMENTS

WO    WO 01/70943 A2    9/2001

OTHER PUBLICATIONS

Komurian-Pradel et al., Brief communication. Strand specific quantitative real-time PCR to study replication of hepatitis C virus genome. Journal of Virology Methods, 116, 103-106, 2004.*
Craggs et al., Development of a strand-specific RT-PCR based assay to detect the replicative form of hepatitis C virus RNA. Journal of Virology Methods, 94, 111-120, 2001.*
Luehrsen et al., Analysis of Differential Display RT-PCR Products Using Fluorescent Primers and GENESCAN™ Software. BioTechniques, 22, 168-174,1997.*
Dowton, et al., "Direct sequencing of double-stranded PCR products without intermediate fragment purification; digestion with mung bean nuclease", Nucleic Acids Research, vol. 21, No. 15, Jul. 25, 1993, pp. 3599-3600.

* cited by examiner

*Primary Examiner* — Frank Lu
(74) *Attorney, Agent, or Firm* — Seyfarth Shaw LLP

(57) ABSTRACT

The invention relates to a method for the quantification of one or more nucleic acids in a sample, for example: making a sample available which contains at least one nucleic acid to be quantified, adding an oligonucleotide probe, the oligonucleotide probe comprising a sequence which can specifically hybridize to the nucleic acid to be quantified or to a common sequence of the nucleic acids to be quantified, incubating the sample under conditions which allow the hybridization of the oligonucleotide probe to the nucleic acid(s) to be quantified, incubating the sample under conditions which allow the extension of hybridized probes, the nucleic acid(s) serving as a template in each case, removing the non-hybridized probes from the sample and quantifying the hybridized oligonucleotide probes to measure the quantity of the nucleic acid(s) to be quantified. The invention also relates to a kit for carrying out said method.

25 Claims, 5 Drawing Sheets

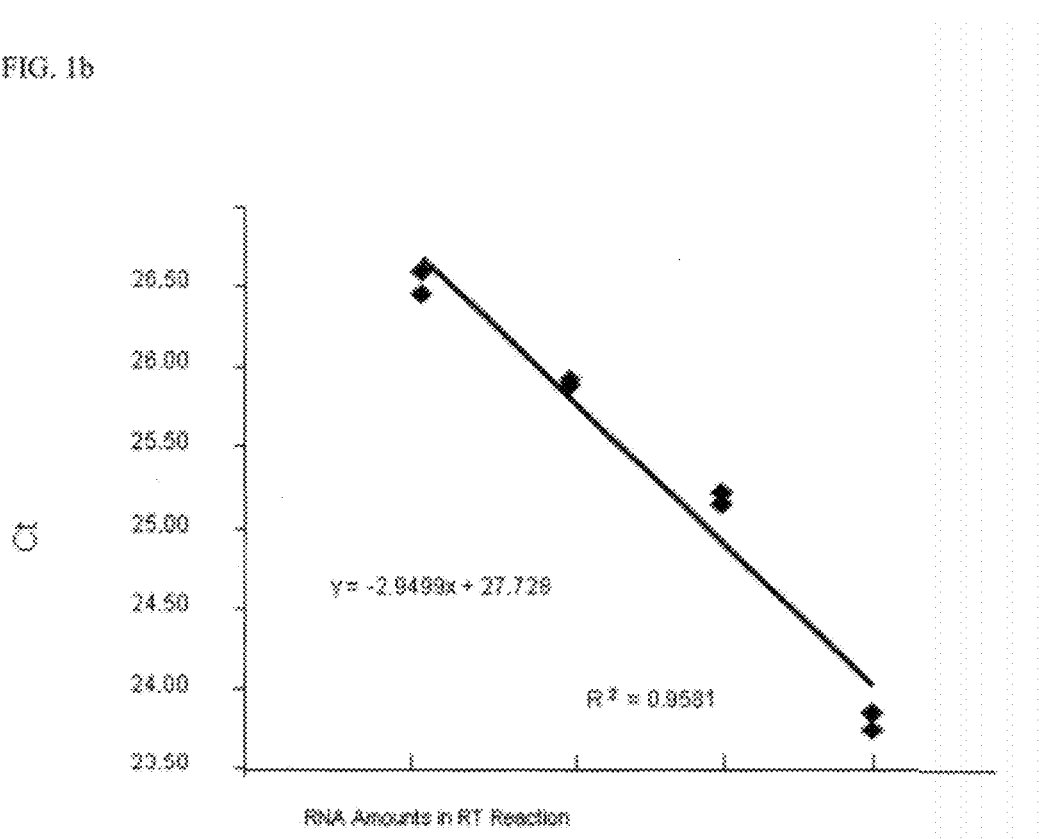

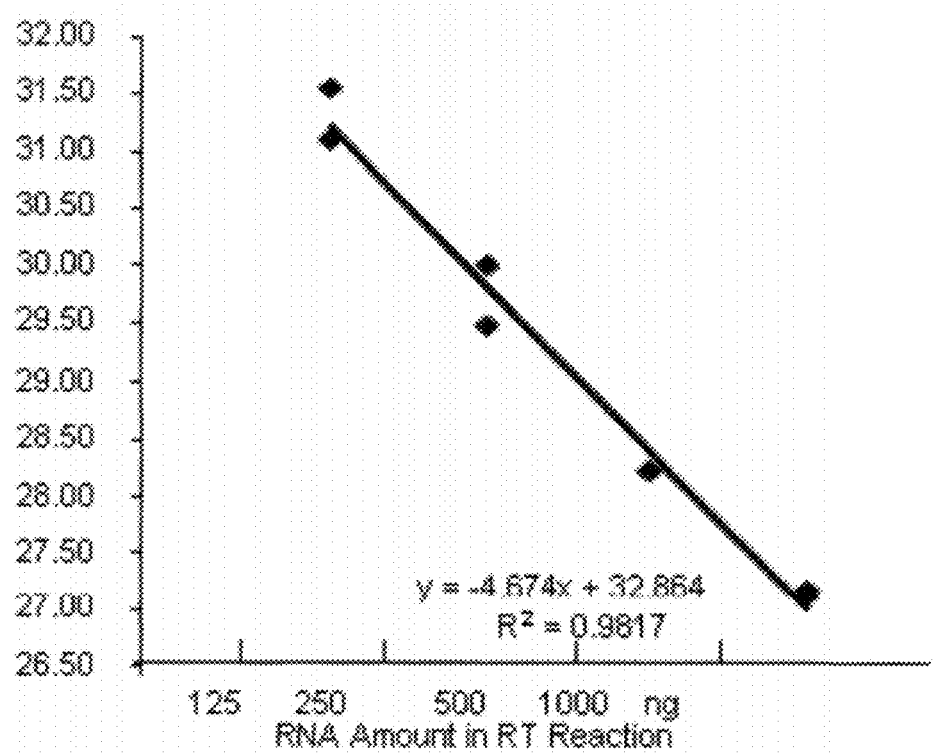

SEQUENCE LISTING

<160> NUMBER OF SEQ ID NOS: 3

<210> SEQ ID NO 1
<211> LENGTH: 100
<212> TYPE: DNA
<213> ORGANISM: Artificial Sequence
<220> FEATURE:
<223> OTHER INFORMATION: OligoAmp

<400> SEQUENCE: 1
caccacgtaa gacataaaac ggccacataa cttggcttta atggacctcc aattttgagt    60

```
gtggtgccat gtaaggatga atgttttttt tttttttttt                            100

<210> SEQ ID NO 2
<211> LENGTH: 22
<212> TYPE: DNA
<213> ORGANISM: Artificial Sequence
<220> FEATURE:
<223> OTHER INFORMATION: AmpliF, Forward primers for amplification of
      OligoAmp

<400> SEQUENCE: 2
caccacgtaa gacataaaac gg                                                22

<210> SEQ ID NO 3
<211> LENGTH: 23
<212> TYPE: DNA
<213> ORGANISM: Artificial Sequence
<220> FEATURE:
<223> OTHER INFORMATION: AmpliR, Reverse primer for the amplification of
      OligoAmp

<400> SEQUENCE: 3
acattcatcc ttacatggca cca                                               23
```

QUANTIFICATION OF NUCLEIC ACIDS

CROSS-REFERENCE TO RELATED APPLICATION

This application is a National Stage of PCT/EP2010/052989, filed Mar. 9, 2010, which claims priority to German Patent Application No. 10 2009 012 039.4, filed Mar. 10, 2009, the disclosures of each which are incorporated herein by reference in their entireties.

The instant application contains a Sequence Listing which has been submitted in ASCII format via EFS-Web and is hereby incorporated by reference in its entirety. Said ASCII copy, created on Dec. 19, 2011, is named 0051_0048_US1_Corrected_Sequence_Listing.txt and is 933 bytes in size.

TECHNICAL FIELD OF THE INVENTION

The present invention relates to the field of biology and chemistry, more particularly molecular biology. In particular, the invention relates to the quantification of nucleic acids by means of oligonucleotide probes and to gene expression analysis, more particularly by means of the polymerase chain reaction (PCR).

BACKGROUND OF THE INVENTION

Quantification of nucleic acids plays an important part in many molecular biology applications, especially in gene expression analysis. Gene expression analyses are used in particular in the fields of basic research, pharmaceutical research, and molecular diagnostics.

In nucleic acid quantification methods, the concentrations and/or relative or absolute amounts of certain nucleic acids in samples are usually determined. In gene expression analysis, the amounts of mRNA and/or cDNA in biological samples are especially relevant. Northern blot, RNase protection assays, competitive reverse transcription PCR, quantitative reverse transcription PCR (qRT-PCR), microarrays, and high-throughput sequencing methods. Quantitative reverse transcription PCR (qRT-PCR) is most commonly used owing to its high specificity, sensitivity, reproducibility, and speed. However, the results are affected by various critical factors owing to the starting amount and the integrity of the mRNA and owing to the effectiveness of the reverse transcriptase and of the polymerase. In order to ensure comparability of gene expression analyses in different samples, it is necessary to carry out normalization of the amounts determined. Common normalization strategies are based on expression analysis of so-called housekeeping genes. Here, it is assumed that the expression of the housekeeping genes does not differ in different samples. However, this assumption is not correct.

Other normalization methods are based on determining the total RNA in the sample, the sample size (cell number or tissue volume), or on introduced foreign RNA. However, all these approaches have their disadvantages. For example, ribosomal RNA makes up a large part of the total RNA in a cell. Therefore, the amount of total RNA is not always representative of the amount of total mRNA. Normalization methods based on cell number or tissue volume do not take into account that different cells may exhibit different transcriptional activities. Also, these methods do not take into account mRNA quality and the effectiveness of the reverse transcriptase and of the polymerase. Although foreign RNA introduced into the sample takes into account the effectiveness of the enzymes during reverse transcription PCR, it does not take into account the amount and quality of the starting mRNA in the sample.

DESCRIPTION OF THE INVENTION

The present invention relates to a quantification method for nucleic acids which, in particular, can be used for gene expression analysis. The quantification method according to the invention makes it possible to take into account not only the amount and quality of the nucleic acids used, but also the effectiveness of the subsequent enzyme reactions. The method according to the invention can also be used for normalization when quantifying particular nucleic acids.

In the method according to the invention, an exogenous oligonucleotide probe is added to a sample which contains the nucleic acid(s) to be quantified. This exogenous oligonucleotide probe comprises a nucleic acid sequence which is not present in the sample, but can bind specifically to the nucleic acid(s) to be quantified. The hybridized oligonucleotide probe is elongated (extended) using a polymerase, with the nucleic acid to be quantified, to which the probe is hybridized, acting as a template. After hybridization and extension of the probe, the probes which did not originally hybridize and are therefore not elongated are removed from the sample, and so the only probes remaining in the sample are those which hybridized to the nucleic acid(s) to be quantified and have therefore been extended. Besides the sequences used for hybridization to the nucleic acid(s) to be quantified ("hybridization sequence"), the oligonucleotide probes may also contain further sequences. Such additional sequences may, for example, be used for quantifying the elongated probes in a PCR reaction ("tag sequence"). The tag sequence is preferably located 5' of the hybridization sequence.

The present invention therefore relates to a method for quantifying one or more nucleic acids in a sample, comprising the following steps:

providing a sample containing at least one nucleic acid to be quantified, adding an oligonucleotide probe to the sample, the oligonucleotide probe comprising a sequence which can specifically hybridize to the nucleic acid to be quantified or to a common sequence of the nucleic acids to be quantified, incubation under conditions which allow hybridization of the oligonucleotide probe to the nucleic acid(s) to be quantified, incubating the sample under conditions which allow extension of hybridized probes, in each case the nucleic acid(s) to be quantified serving as templates, removing the nonhybridized probes from the sample, quantifying the hybridized oligonucleotide probes as a measure of the amount of the nucleic acid(s) to be quantified.

Preferably, extension is carried out using a polymerase, i.e., the sample is incubated with a polymerase under conditions which allow extension of hybridized probes. Therefore, preferably, extension of hybridized probes is carried out using a polymerase.

In the method according to the invention, the only probes quantified are those which have hybridized to another nucleic acid and have accordingly been elongated. They are therefore a measure of the amount of nucleic acid to be quantified. Depending on the sequence of the probe, only specific nucleic acids, or entire groups of nucleic acids which contain a sequence which is largely complementary to the probe, are quantified. Preferably, the sequence of the probe is complementary to a sequence on the nucleic acid(s) to be quantified to an extent of at least 85%, 90%, and most preferably more than 95%.

The nonhybridized and nonelongated probes are removed from the sample prior to quantification of the hybridized oligonucleotide probes. This can be achieved, for example, by enzymatic reactions (e.g., nuclease degradation), chemical reactions, heat, or physical processes, for example chromatographic or electrophoretic methods.

Preferably, the nonhybridized probes are removed using a nuclease which can specifically degrade single-stranded nucleic acids. The nuclease is preferably an exonuclease. The exonuclease is preferably selected from the group consisting of exonuclease I, S1 nuclease, lambda exonuclease, and exonuclease VII.

Oligonucleotides are oligomers made up of few nucleotides, i.e., they are short, preferably single-stranded nucleic acids. Preferably, the oligonucleotides are 10-200 nucleotides, preferably 30-100 nucleotides, preferentially 70-90 nucleotides, in length.

The oligonucleotide probe is a single-stranded oligonucleotide. It is preferably selected from the group consisting of DNA, RNA, PNA, and LNA. In any case, the oligonucleotide probe must be a nucleic acid which can be extended complementarily to the template. Preferably, the oligonucleotide probe is a DNA oligonucleotide.

The oligonucleotide probe can also contain modified nucleobases and/or modified linkers.

In a particular embodiment of the method according to the invention, at least two nucleic acids are quantified and the quantified amounts of at least two nucleic acids are used to form a ratio. This can be achieved, for example, by the use of various oligonucleotide probes which contain different hybridization sequences and tag sequences.

The nucleic acid(s) to be quantified is/are preferably RNA(s) or DNA(s). The nucleic acid(s) to be quantified can be, for example, nucleic acid(s) selected from the group consisting of cDNA (complementary DNA), LNA (locked nucleic acid), mRNA (messenger RNA), mtRNA (mitochondrial RNA), rRNA (ribosomal RNA), tRNA (transfer RNA), nRNA (nuclear RNA), siRNA (short interfering RNA), snRNA (small nuclear RNA), snoRNA (small nucleolar RNA), scaRNA (small Cajal body-specific RNA), microRNA, dsRNA (double-stranded RNA), ribozymes, riboswitches, viral RNA, dsDNA (double-stranded DNA), ssDNA (single-stranded DNA), plasmid DNA, cosmid DNA, chromosomal DNA, viral DNA, mtDNA (mitochondrial DNA), nDNA (nuclear DNA), snDNA (small nuclear DNA). The nucleic acid(s) to be quantified can also be all the members of a group of nucleic acids, preferably all mRNAs in the sample ("total mRNA") or all cDNAs in the sample ("total cDNA").

In a preferred embodiment of the method according to the invention, the nucleic acid(s) to be quantified is/are mRNA (s) or cDNA(s).

The common sequence of the nucleic acid(s) to be quantified can be, for example, a poly(A) sequence, for example the poly(A) tail of mRNA. In the case of cDNA, the common sequence is preferably poly(dT).

It is particularly preferred for the nucleic acid(s) to be quantified to be mRNA and for the common sequence to be a poly(A) sequence.

It is also preferred for the nucleic acid(s) to be quantified to be cDNA and for the common sequence to be a poly(dT) sequence.

So that hybridization to poly(A) or poly(dT) sequences is possible, the oligonucleotide probe must contain a poly(T) or poly(dT), or poly(A) or poly(dA), sequence.

Therefore, in one embodiment, it is preferred for the oligonucleotide probe to contain a poly(T) or poly(dT) sequence.

In another embodiment, it is preferred for the oligonucleotide probe to contain a poly(A) or poly(dA) sequence.

The poly(dT), poly(T), poly(dA), and poly(A) sequences are preferably located at the 3' end of the oligonucleotide probe. Preferably, the poly(dT), poly(T), poly(dA), and poly(A) sequences are between 8 and 100, particularly preferably between 10 and 20, nucleotides in length.

As described above, in a preferred embodiment, the oligonucleotide probe contains a tag sequence. Particularly preferred tag sequences are sequences which have no homologies in eukaryotic genomes.

Quantification of the hybridized oligonucleotide probe is preferably carried out by means of quantitative PCR. For example, for this purpose, quantification of the tag sequence is carried out by means of quantitative PCR.

The oligonucleotide probe can be used as a primer for reverse transcription of mRNA into cDNA in an RT-PCR. The resulting cDNA can be quantified by means of quantitative PCR (qPCR).

When the nucleic acid to be quantified is DNA, quantification of the hybridized probe can be carried out directly via qPCR.

The DNA polymerase which is used during quantitative (real-time) PCR is preferably a polymerase from a thermophilic organism or is a thermostable polymerase or is a polymerase selected from the group consisting of *Thermus thermophiles* (Tth) DNA polymerase, *Thermus acquaticus* (Taq) DNA polymerase, *Thermotoga maritima* (Tma) DNA polymerase, *Thermococcus litoralis* (Tli) DNA polymerase, *Pyrococcus furiosus* (Pfu) DNA polymerase, *Pyrococcus woesei* (Pwo) DNA polymerase, *Pyrococcus kodakaraensis* KOD DNA polymerase, *Thermus filiformis* (Tfi) DNA polymerase, *Sulfolobus solfataricus* Dpo4 DNA polymerase, *Thermus pacificus* (Tpac) DNA polymerase, *Thermus eggertsonii* (Teg) DNA polymerase, *Thermus brockianus* (Tbr) and *Thermus flavus* (Tfl) DNA polymerase.

When RNA, for example mRNA, is to be quantified, the RNA has to be reverse transcribed into DNA. This is achieved with an enzyme having reverse transcriptase activity. Such enzymes can be, for example, reverse transcriptases from viruses, bacteria, archaebacteria, and eukaryotes, more particularly from thermostable organisms. These also include, for example, enzymes from introns, retrotransposons, or retroviruses. According to the invention, an enzyme having reverse transcriptase activity is an enzyme which is capable, under appropriate buffer conditions, of incorporating deoxyribonucleotides in a complementary manner at a ribonucleic acid at the 3' end of a deoxyoligonucleotide or ribooligonucleotide hybridized to the ribonucleic acid. This comprises not only enzymes which naturally have this function, but also enzymes which acquire such a function only as a result of alteration of their gene sequence, such as mutagenesis for example, or as a result of appropriate buffer conditions.

Preferably, the enzyme having reverse transcriptase activity is an enzyme which is selected from the group comprising HIV reverse transcriptase, M-MLV reverse transcriptase, EAIV reverse transcriptase, AMV reverse transcriptase, *Thermus thermophilus* DNA polymerase I, M-MLV RNase H, Superscript, Superscript II, Superscript III, Monsterscript (Epicentre), Omniscript, Sensiscript Reverse Transcriptase (Qiagen), ThermoScript and Thermo-X (both Invitrogen). According to the invention, use can also be made of enzymes which, as enzyme, have reverse transcriptase activity only after modification of the gene sequence. Use can also be made of reverse transcriptase activity which has increased fidelity. By way of example, mention may be made here of, for example, AccuScript reverse transcriptase (Stratagene). It is obvious to a person skilled in the art that the use of mixtures of two or more enzymes having reverse transcriptase activity is also possible.

It is known to a person skilled in the art that most enzymes having reverse transcriptase activity require a divalent ion. Thus, in a preferred embodiment, there is a divalent ion for those enzymes which require a divalent ion. $Mg^{2+}$, $Mn^{2+}$ are preferred.

Preferred combinations of enzymes are HIV reverse transcriptase or M-MLV reverse transcriptase or EAIV reverse transcriptase or AMV reverse transcriptase or *Thermus thermophilus* DNA polymerase I or M-MLV RNase H, Superscript, Superscript II, Superscript III or Monsterscript (Epicentre) or Omniscript Reverse Transcriptase (Qiagen) or Sensiscript Reverse Transcriptase (Qiagen), ThermoScript, Thermo-X (both Invitrogen) or a mixture of two or more enzymes having reverse transcriptase activity and poly(A) polymerase from *Escherichia coli*. Also, HIV reverse transcriptase or M-MLV reverse transcriptase or EAIV reverse transcriptase or AMV reverse transcriptase or *Thermus thermophiles* DNA polymerase I or M-MLV RNase H, Superscript, Superscript II, Superscript III or Monsterscript (Epicentre) or Omniscript Reverse Transcriptase (Qiagen) or Sensiscript Reverse Transcriptase (Qiagen), ThermoScript, Thermo-X (both Invitrogen) or a mixture of two or more enzymes having reverse transcriptase activity and poly(A) polymerase from yeast.

In quantitative (real-time) PCR, use can be made of fluorescently labeled primers and/or probes, for example LightCycler probes (Roche), TaqMan probes (Roche), Molecular Beacons, Scorpion primers, Sunrise primers, LUX primers, or Amplifluor primers. Probes and/or primers can contain, for example, covalently or noncovalently bound fluorescent dyes, for example fluorescein isothiocyanate (FITC), 6-carboxyfluorescein (FAM), xanthene, rhodamine, 6-carboxy-2',4',7',4,7-hexachlorofluorescein (HEX), 6-carboxy-4',5'-dichloro-2',7'-dimethodyfluorescein (JOE), N,N,N',N'-tetramethyl-6-carboxyrhodamine (TAMRA), 6-carboxy-X-rhodamine (ROX), 5-carboxyrhodamine 6G (R6G5), 6-carboxyrhodamine 6G (RG6), rhodamine 110; coumarins, such as umbelliferones, benzimides, such as Hoechst 33258; phenanthridines, such as Texas Red, ethidium bromide, acridine dyes, carbazole dyes, phenoxazine dyes, porphyrin dyes, polymethine dyes, cyanine dyes, such as Cy3, Cy5, Cy7, BODIPY dyes, quinoline dyes, and Alexa dyes.

A person skilled in the art is aware of the appropriate conditions for quantitative PCR or quantitative reverse transcription PCR. These concern, for example, primer design, the selection of appropriate processing temperatures (reverse transcription, denaturation, primer annealing, elongation), the number of PCR cycles, the buffer conditions. Reverse transcription and Besides PCR, other amplification methods can also be used, and these can be selected from the group comprising rolling circle amplification (as described in Liu et al., "Rolling circle DNA synthesis: small circular oligonucleotides as efficient templates for DNA polymerases", J. Am. Chem. Soc. 118: 1587-1594 (1996)), isothermal amplification (as described in Walker et al., "Strand displacement amplification—an isothermal, in vitro DNA amplification technique", Nucleic Acids Res. 20(7): 1691-6 (1992)), the ligase chain reaction (as described in Landegren et al., "A ligase-mediated gene detection technique", Science 241: 1077-1080, 1998, or in Wiedmann et al., "Ligase chain reaction (LCR)— overview and applications", PCR Methods and Applications (Cold Spring Harbor Laboratory Press, Cold Spring Harbor Laboratory, NY, 1994), pages S51-S64). However, the polymerase chain reaction (PCR) is preferred.

The invention likewise relates to a kit for nucleic acid quantification, comprising:
at least one nuclease, preferably exonuclease,
optionally dNTPs (preferably as a solution of a mixture of dCTP, dATP, dGTP, and dTTP (e.g., 5 mM each, dNTP mix)),
optionally a buffer solution or a stock buffer solution,
a DNA polymerase,
optionally a reverse transcriptase,
an oligonucleotide probe, comprising a tag sequence and a sequence which can specifically hybridize to the nucleic acid to be quantified or to a common sequence of the nucleic acids to be quantified,
primer and/or a second oligonucleotide probe which can hybridize to the tag sequence.

What is described above for the method according to the invention applies to the polymerases, reverse transcriptases, oligonucleotide probes, and primers of the kit according to the invention.

The kits and method according to the invention can be used to analyze gene expression in a biological sample.
Sequences

```
SEQ ID NO: 1: OligoAmp
5'-CACCACGTAAGACATAAAACGGCCACATAACTTGGCTTTAATGGAC

CTCCAATTTTGAGTGTGGTGCCATGTAAGGATGAATGTTTTTTTTTTT

TTTTT-3'

SEQ ID NO: 2: AmpliF, forward primer for the
amplification of OligoAmp
5'-CACCACGTAAGACATAAAACGG-3'

SEQ ID NO: 3: AmpliR, reverse primer for the
amplification of OligoAmp
5'-ACATTCATCCTTACATGGCACCA-3'
```

DESCRIPTION OF THE FIGURES

FIG. 1*b*: Quantification of the OligoAmp oligo by qPCR, after reverse transcription and Exol digestion. Diagram of Ct values versus RNA amounts in RT.

FIG. 3*b*: Quantification of the endogenous TBP gene by qPCR, after reverse transcription and Exol digestion. Diagram of Ct values versus RNA amounts in RT.

EXAMPLES

Example 1

Reverse transcriptase reactions were carried out using Omniscript (Qiagen) according to the manufacturer's instructions. The reverse transcriptase reactions contained the following components: total RNA from Ramos human Burkitt's lymphoma cells as templates (1 µg, 500 ng, 250 ng, 125 ng, and 0 ng); oligonucleotides, OligoAmp (0.1 nM final concentration) having the nucleotide sequence SEQ ID NO:1 as reverse transcriptase primer; reverse transcriptase, Omniscript; dNTPs, RNase inhibitor; reverse transcriptase buffer and RNase-free water. The sequence of OligoAmp comes from the potato genome and has no homologs in the human genome.

18 µl of each reverse transcription product were then admixed with, in each case, 2 µl of exonuclease I (20 U/µl, Epicentre) or water (as non-exonuclease-treated control), and subjected to digestion at 37° C. for 60 minutes. After digestion, the exonuclease I was inactivated at 95° C. for 10 minutes. 2 µl of each exonuclease I reaction mixture or of the template-free controls were mixed with QuantiFast SYBR Green Mix (Qiagen) and specific primers in order to quantify the undigested OligoAmps. The sequences of the primers used in the qPCR, AmpliF and AmpliR, are shown under SEQ ID NO:2 and SEQ ID NO:3.

Figure 1A:
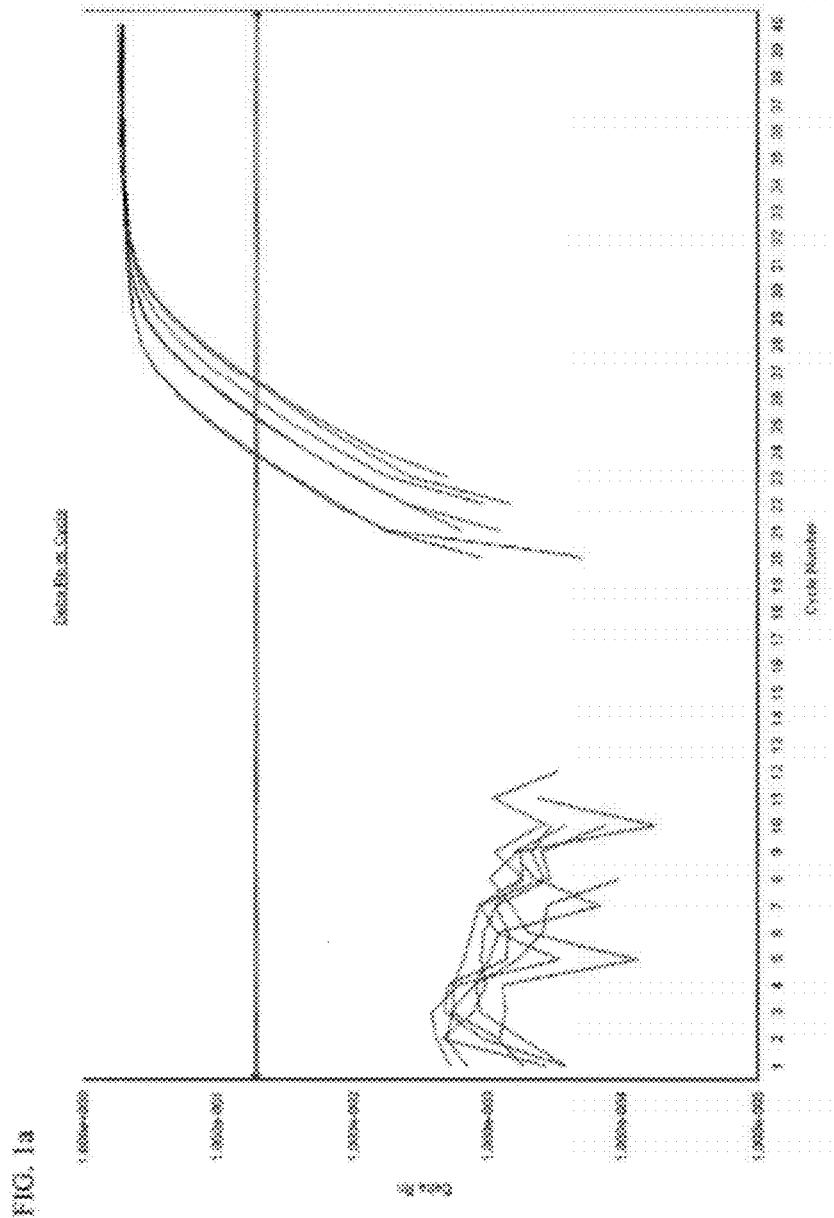
FIG. 1*a*: Quantification of the OligoAmp oligo by qPCR, after reverse transcription and Exol digestion. Amplification plot.

It is apparent from the amplification plot in FIG. 1a and table 1 that, after reverse transcription and exonuclease treatment, different amounts of remaining OligoAmp were detected and quantified. As expected, in the reactions with higher starting amounts of RNA, larger amounts of Oligo-Amp were protected from exonuclease degradation and therefore remained undigested. This is reflected in lower Ct values in the qPCR. The Ct values and the logarithm of the starting amount of RNA show a good linear correlation.

TABLE 1

Quantification of the OligoAmp oligo by qPCR, after reverse transcription and ExoI digestion.

| OligoAmp concentration (nM) | RNA in RT (ng) | RNA (ng) in qPCR | log (RNA in PCR) | Ct | Ct, mean |
|---|---|---|---|---|---|
| 0.1 | 1000 | 18 | 1.26 | 23.75 | 23.81 |
|  |  | 18 | 1.26 | 23.86 |  |
|  | 500 | 9 | 0.95 | 25.22 | 25.19 |
|  |  | 9 | 0.95 | 25.16 |  |
|  | 250 | 4.5 | 0.65 | 25.93 | 25.91 |
|  |  | 4.5 | 0.65 | 25.89 |  |
|  | 125 | 2.25 | 0.35 | 26.59 | 26.53 |
|  |  | 2.25 | 0.35 | 26.46 |  |

Consolidation of the Ct values.

Figure 2:
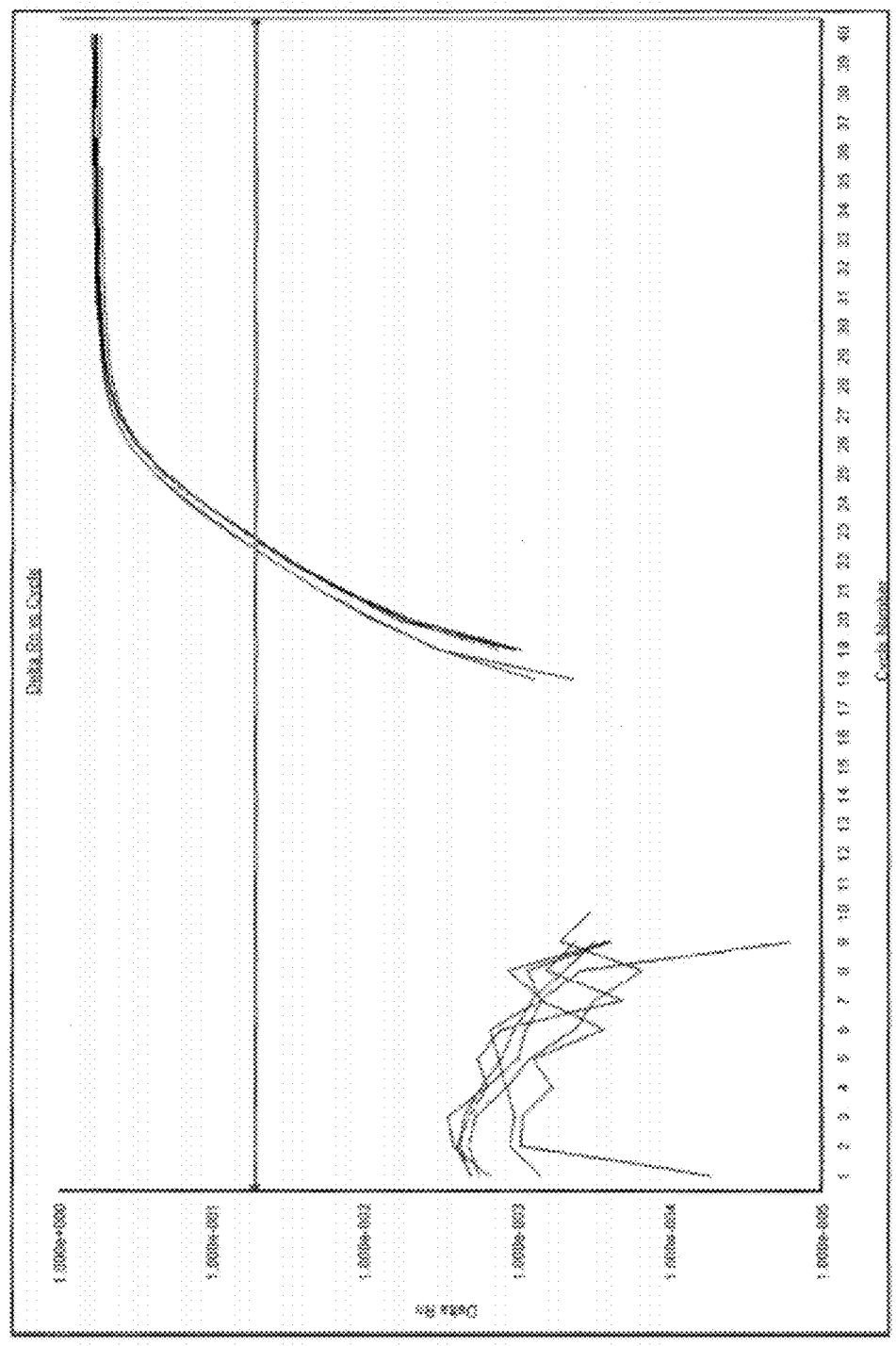
FIG. 2: Quantification of the OligoAmp oligos by qPCR, after reverse transcription, without Exol digestion. Amplification plot.

In contrast to the reverse transcription products treated with exonuclease I, the OligoAmp oligonucleotides in the water control samples were all detected with similar Ct values, irrespective of the starting amount of RNA (see FIG. 2, table 2).

TABLE 2

Quantification of the OligoAmp oligos by qPCR, after reverse transcription, without ExoI digestion.

| OligoAmp concentration (nM) | RNA in RT (ng) | RNA (ng) in RT | log (RNA in PCR) | Ct | Ct, mean |
|---|---|---|---|---|---|
| 0.1 | 1000 | 18 | 1.26 | 22.49 | 22.49 |
|  |  | 18 | 1.26 | 22.48 |  |
|  | 500 | 9 | 0.95 | 22.72 | 22.67 |
|  |  | 9 | 0.95 | 22.62 |  |
|  | 250 | 4.5 | 0.65 | 22.70 | 22.77 |
|  |  | 4.5 | 0.65 | 22.84 |  |
|  | 125 | 2.25 | 0.35 | 22.60 | 22.65 |
|  |  | 2.25 | 0.35 | 22.70 |  |

Consolidation of the Ct values.

Figure 3A:
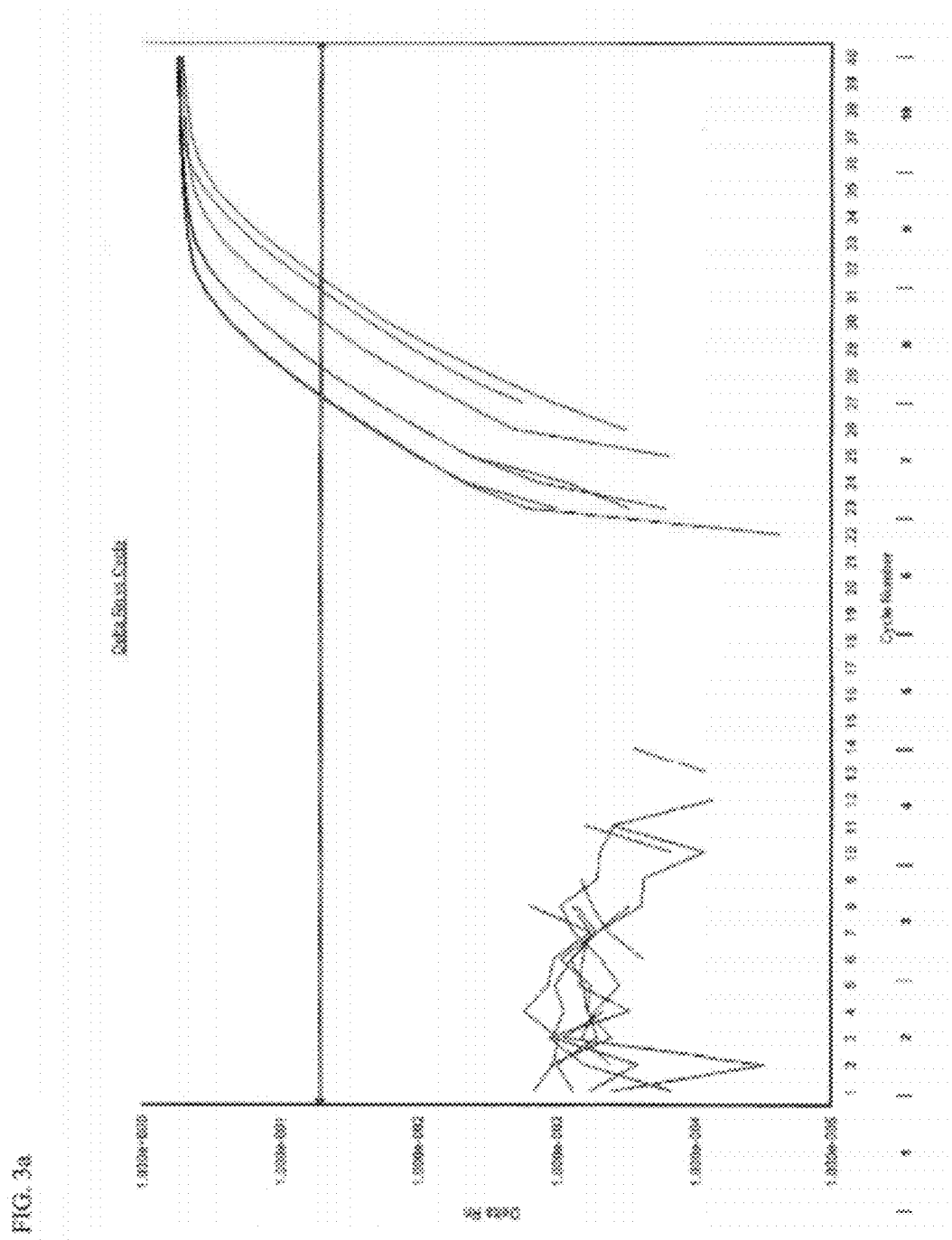
FIG. 3*a*: Quantification of the endogenous TBP gene by qPCR, after reverse transcription and Exol digestion. Amplification plot.

In the same reverse transcriptase reaction, it was possible, with a high degree of confidence, for endogenous genes to be reverse transcribed and subsequently quantified using qPCR. This is shown in FIGS. 3a and 3b and in table 3.

TABLE 3

Quantification of the endogenous TBP gene by qPCR, after reverse transcription and ExoI digestion.

| OligoAmp concentration (nM) | RNA in RT (ng) | RNA (ng) in RT | log (RNA in PCR) | Ct | Ct, mean |
|---|---|---|---|---|---|
| 0.1 | 1000 | 18 | 1.26 | 22.49 | 22.49 |
|  |  | 18 | 1.26 | 22.48 |  |
|  | 500 | 9 | 0.95 | 22.72 | 22.67 |
|  |  | 9 | 0.95 | 22.62 |  |
|  | 250 | 4.5 | 0.65 | 22.70 | 22.77 |
|  |  | 4.5 | 0.65 | 22.84 |  |
|  | 125 | 2.25 | 0.35 | 22.60 | 22.65 |
|  |  | 2.25 | 0.35 | 22.70 |  |

Consolidation of the Ct values.

The exonuclease I-treated reverse transcription products were used as templates in the SYBR Green-based qPCR (QuantiFast SYBR Green, Qiagen). TBP-specific cDNA primers were used for amplification in the qPCR.

The present data show that the quantification method using mRNA-binding, nuclease-resistant exogenous oligonucleotides can be used as part of the normalization strategy in order to check the starting amount of mRNA and the efficiency of reverse transcription and of PCR.

The invention claimed is:

1. A method for quantifying nucleic acid in a sample, comprising:
   (a) providing a sample comprising nucleic acid to be quantified;
   (b) adding a sufficient amount of a single-stranded oligonucleotide probe having a length of about 70 to about 100 nucleotides to the sample, thereby forming a probe-nucleic acid sample, the single-stranded oligonucleotide probe comprising a hybridization sequence and a 5' tag sequence, wherein the hybridization sequence can specifically hybridize to the nucleic acid to be quantified with at least 90% complementarity, and wherein the 5' tag sequence is located 5' of the hybridization sequence;
   (c) incubating the probe-nucleic acid sample from step (b) under conditions which allow hybridization of the hybridization sequence of the single-stranded oligonucleotide probe to the nucleic acid to be quantified, thereby forming a hybridized nucleic acid sample;
   (d) incubating the hybridized nucleic acid sample from step (c) under conditions which allow extension of the single-stranded oligonucleotide probe hybridized to the nucleic acid to be quantified, thereby forming an extended oligonucleotide probe;
   (e) after step (d), removing any of the single-stranded oligonucleotide probe added in step (b) and not hybridized to the nucleic acid to be quantified in step (c); and
   (f) following step (e), measuring an amount of the nucleic acid to be quantified in the sample by quantifying the extended oligonucleotide probe, wherein said quantifying the extended oligonucleotide probe comprises amplifying the 5' tag sequence of the extended oligonucleotide probe using a primer that can hybridize to the 5' tag sequence.

2. The method as claimed in claim 1, wherein the extension of the single-stranded oligonucleotide probe hybridized to the nucleic acid to be quantified is carried out using a polymerase.

3. The method as claimed in claim 1, wherein step (e) is performed using a nuclease which can specifically degrade single-stranded nucleic acids.

4. The method as claimed in claim 3, wherein the nuclease is an exonuclease.

5. The method as claimed in claim 4, wherein the exonuclease is selected from exonuclease 1, S1 nuclease, lambda exonuclease, and exonuclease VII.

6. The method as claimed in claim 1, wherein the oligonucleotide probe is selected from DNA, RNA, and locked nucleic acid (LNA).

7. The method as claimed in claim 6, wherein the oligonucleotide probe contains modified nucleobases and/or modified linkers.

8. The method as claimed in claim 1, wherein the nucleic acid comprises at least two specific nucleic acids, further comprising adding at least two specific oligonucleotide probes which specifically hybridize to the at least two specific nucleic acids and contain different hybridization sequences and tag sequences to the sample, and quantifying the amount of each of the at least two specific nucleic acids in the sample using steps (c) to (f) of claim 1, and calculating a ratio of the at least two specific nucleic acids in the sample based on the amount of each of the at least two specific nucleic acids in the sample.

9. The method as claimed in claim 1, wherein the nucleic acid to be quantified is RNA or DNA.

10. The method as claimed in claim 9, wherein the RNA is mRNA and the DNA is cDNA.

11. The method as claimed in claim 10, wherein the nucleic acid to be quantified is mRNA having a common sequence consisting of a poly(A) sequence.

12. The method as claimed in claim 10, wherein the nucleic acid to be quantified is cDNA having a common sequence consisting of a poly(dT) sequence.

13. The method as claimed in claim 11, wherein the oligonucleotide probe contains a poly(T) or poly(dT) sequence.

14. The method as claimed in claim 12, wherein the oligonucleotide probe contains a poly(A) or poly(dA) sequence.

15. The method as claimed in claim 1, wherein said quantifying the extended oligonucleotide probe is carried out by quantitative PCR.

16. The method as claimed in claim 15, wherein the nucleic acid to be quantified is mRNA, and an oligonucleotide probe is used as a primer for reverse transcription of the mRNA into cDNA using RT-PCR.

17. The method as claimed in claim 1, wherein the oligonucleotide probe contains a fluorescent dye.

18. The method of claim 1, wherein the nucleic acid to be quantified is cDNA, and wherein a common sequence of the cDNA is a poly(dT) sequence, and the hybridization sequence of the single-stranded oligonucleotide probe comprises a poly (A) sequence or a poly(dA) sequence.

19. The method of claim 18, wherein said quantifying the extended oligonucleotide probe in step (f) is carried out by quantitative PCR.

20. The method of claim 1, wherein the least 90% complementarity is more than 95% complementarity.

21. A method for quantifying nucleic acid in a sample, comprising:
 (a) providing a sample comprising nucleic acid to be quantified, wherein the nucleic acid to be quantified is mRNA or cDNA;
 (b) adding a sufficient amount of a single-stranded oligonucleotide probe having a length of about 70 to about 100 nucleotides to the sample, thereby forming a probe-mRNA or probe-cDNA sample, the single-stranded oligonucleotide probe comprising a hybridization sequence and a 5' tag sequence, wherein the hybridization sequence can specifically hybridize to a common sequence of the mRNA or a common sequence of the cDNA with at least 90% complementarity, and wherein the 5' tag sequence is located 5' of the hybridization sequence;
 (c) incubating the probe-mRNA or probe-cDNA sample from step (b) under conditions which allow hybridization of the hybridization sequence of the single-stranded oligonucleotide probe to the mRNA or the cDNA, thereby forming a hybridized mRNA or cDNA sample;
 (d) incubating the hybridized mRNA or cDNA sample from step (c) under conditions which allow extension of the single-stranded oligonucleotide probe hybridized to the mRNA or the cDNA, thereby forming an extended oligonucleotide probe;
 (e) after step (d), removing any of the single-stranded oligonucleotide probe added in step (b) and not hybridized to the mRNA or cDNA in step (c); and
 (f) following step (e), measuring an amount of the mRNA or cDNA in the sample by quantifying the extended oligonucleotide probe, wherein said quantifying the extended oligonucleotide probe comprises amplifying the 5' tag sequence of the extended oligonucleotide probe using a primer that can hybridize to the 5' tag sequence.

22. The method of claim 21, wherein the nucleic acid to be quantified is mRNA, and wherein the common sequence of the mRNA is a poly(A) sequence, and the hybridization sequence of the single-stranded oligonucleotide probe comprises a poly(T) sequence or a poly(dT) sequence.

23. The method of claim 22, wherein said quantifying the extended oligonucleotide probe in step (f) is carried out by quantitative PCR.

24. The method of claim 22, wherein the extension of the single-stranded oligonucleotide probe hybridized to the mRNA or the cDNA in step (d) is carried out with an enzyme having reverse transcriptase activity.

25. The method of claim 21, wherein the least 90% complementarity is more than 95% complementarity.

* * * * *